United States Patent [19]

Muramatsu et al.

[11] Patent Number: 4,468,289

[45] Date of Patent: Aug. 28, 1984

[54] COULOMETRIC TITRATION METHOD

[75] Inventors: Kozo Muramatsu, Machida; Masanori Hirai, Kawasaki; Saburo Sugihara; Hirozumi Nakamura, both of Chigasaki, all of Japan

[73] Assignee: Mitsubishi Kasai Kogyo Kabushiki Kaisha, Tokyo, Japan

[21] Appl. No.: 231,013

[22] Filed: Feb. 3, 1981

[30] Foreign Application Priority Data

Feb. 12, 1980 [JP] Japan .................................. 55-15736

[51] Int. Cl.³ .......................................... G01N 27/44
[52] U.S. Cl. .................................... 204/1 T; 204/405
[58] Field of Search .......... 204/1 T, 1 M, 1 F, 195 T, 204/195 R; 23/230 R, 232 E

[56] References Cited

U.S. PATENT DOCUMENTS

| 2,624,701 | 1/1953 | Austin | 204/195 T |
| 2,928,782 | 3/1960 | Leisey | 204/195 T |
| 3,305,468 | 2/1967 | Liesch | 204/195 T |
| 3,499,733 | 3/1970 | Abbott et al. | 204/195 T |

Primary Examiner—T. Tung
Attorney, Agent, or Firm—Oblon, Fisher, Spivak, McClelland & Maier

[57] ABSTRACT

In a coulometric titration method, during a preparation step before a titration step a composition to be titrated is accumulated in an electrolyte.

5 Claims, 4 Drawing Figures

COULOMETRIC TITRATION METHOD

BACKGROUND OF THE INVENTION

This invention relates to a coulometric titration method, more particularly a coulometric titration method capable of measuring a minute quantity of substance at high accuracies.

An electric titration method has been well known comprising the steps of introducing into a titration cell a composition to be titrated in a sample or after converting the composition into a titratable compound, together with a carrier gas, passing electric current between opposing generating electrodes disposed in the titration cell so as to eliminate a potential variation of an electrolyte contained in the cell caused by the introduction of the composition to be titrated, integrating the electric current and calculating the quantity of the composition to be titrated from the integrated value according to the law of Faraday. With this method, however, it is necessary to bring the apparatus to a stable state by passing the carrier gas through the apparatus prior to the measuring. Even in this step, since the potential of the electrolyte varies slightly, it is necessary to maintain the potential of the electrolyte at a preset potential, i.e., an end potential by passing across the electrodes a current proportional to the difference between the potential of the electrolyte detected by a detecting electrode and the end potential.

As the apparatus becomes stable, the current flowing through the generating electrodes becomes a constant value, termed a blank current.

The sample is injected into or admixed with the carrier gas and the resulting mixture is introduced into the electrolyte directly or after converting the sample into an electrolizable compound. Then, as the potential of the detecting electrode varies, a titration current proportional to the difference between the detected potential and the end potential is passed across the generating electrodes so as to restore the detected potential to the end potential. A condition in which the detected potential reaches a value before sample introduction is taken as the completion of the titration and the difference between the titration current passed across the generating electrodes during the titration and the blank current is integrated to calculate the quantity of the composition to be titrated.

When the sample is introduced at a constant rate, the composition to be titrated is introduced into the electrolyte thus increasing the potential thereof. However, since the composition to be titrated in the electrolyte is immediately consumed as a result of the titration, the potential of the electrolyte would be maintained at a value slightly higher than the end point potential while the component to be titrated is being introduced. Accordingly, the current is also maintained at a value slightly higher than the blank current in proportion to the variation in the potential. Upon completion of the introduction of the sample, the quantity of the component introduced decreases so that the current also decreases back to the blank current.

Although this method is used widely, when the injected quantity of the composition to be titrated is small, the blank current becomes large relative to the titration current thus degrading the accuracy of measurement.

SUMMARY OF THE INVENTION

It is an object of this invention to provide an improved coulometric titration method capable of accurately titrating a sample containing very small quantity of composition to be titrated.

According to this invention, there is provided a coulometric titration method, characterized by comprising the steps of: a balancing step in which an electrolyte potential in a titration cell is detected while passing carrier gas, and current is passed between generating electrodes immersed in the electrolyte so as to eliminate potential difference between the detected potential and a preset potential; a waiting step in which a constant current not depending upon the electrolyte potential is passed between the generating electrodes; a titration step in which the electrolyte potential is measured and current is passed between the generating electrodes so as to eliminate potential difference between the detected potential and the set potential; a step of beginning introduction of a composition to be titrated into the titration cell together with the carrier gas during the waiting step; a step of integrating a difference between current flowing between the generating electrodes during the titration step and a blank current; and a step of calculating a quantity of the composition to be titrated introduced into the titration cell in accordance with an integrated value.

DESCRIPTION OF THE PREFERRED EMBODIMENT

Figure 1:
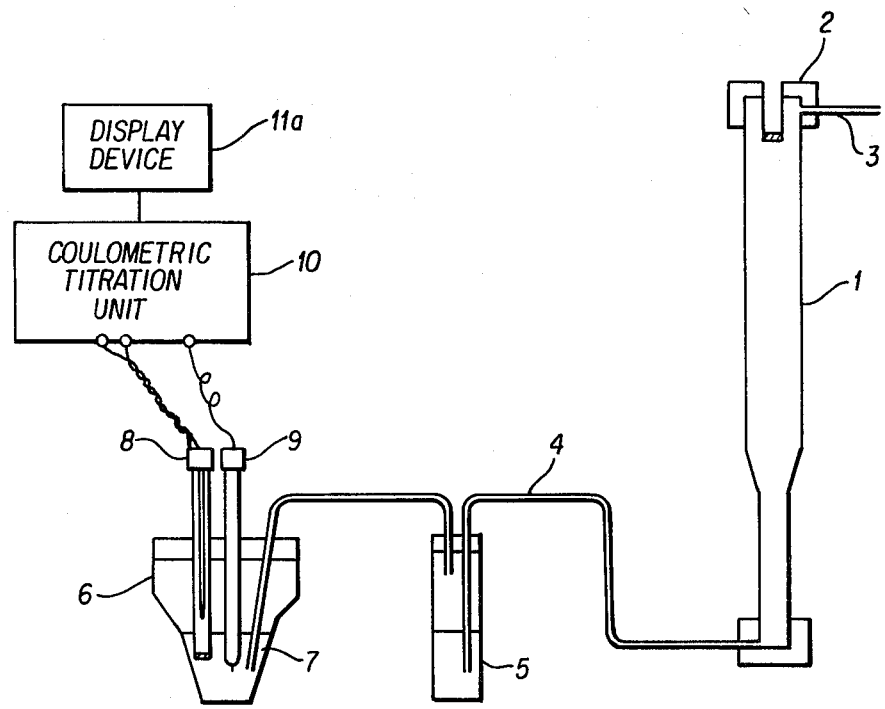
FIG. 1 is a diagrammatic representation showing one example of a coulometric titration apparatus utilized to carry out the method of this invention.

Apparatus shown in FIG. 1 and utilized to carry out the method of this invention comprises a reaction tube 1 supplied with carrier gas from a source thereof, not shown, through a gas conduit 3. If necessary, a suitable catalyst is packed in the reaction tube and a sample is introduced thereinto via a sample admission port 2. Usually, the sample is introduced at a constant rate of from 0.2–1.2 $\mu$l/second, and the total quantity of the sample introduced is about 20–200 $\mu$l.

The gas in the reaction tube 1 is introduced into an electrolyte 7 contained in a titration cell 6 via conduit 4. In the electrolyte 7 are dipped a pair of generating electrodes 8 and a detection electrode 9, the former being connected to a current source and a current integrator, and the latter to a potential detector. In FIG. 1, the current source, the current integrator and the potential detector are generally designated as a coulometric titration unit 10. A display device 11a is provided for displaying the integrated current. A dehumidifier 5 is included in the conduit 4 to remove excess moisture where the sample contains a large quantity of water or when the reaction effected in the reaction tube 1 produces a large quantity of water.

In the absence of the dehumidifier 5, moisture will be admitted into the electrolyte together with the carrier gas and condenses in the electrolyte to generate heat of condensation, thus increasing the temperature of the electrolyte. Then, as is clear from Nernst's equation, the potential of the electrolyte varies resulting in a measurement error. As the dehumidifier may be used a small air washing bottle charged with such reagent as sulfuric acid, phosphoric acid, or caustic soda solution, etc. which absorbs moisture but freely passes the composition to be titrated.

Figure 2:
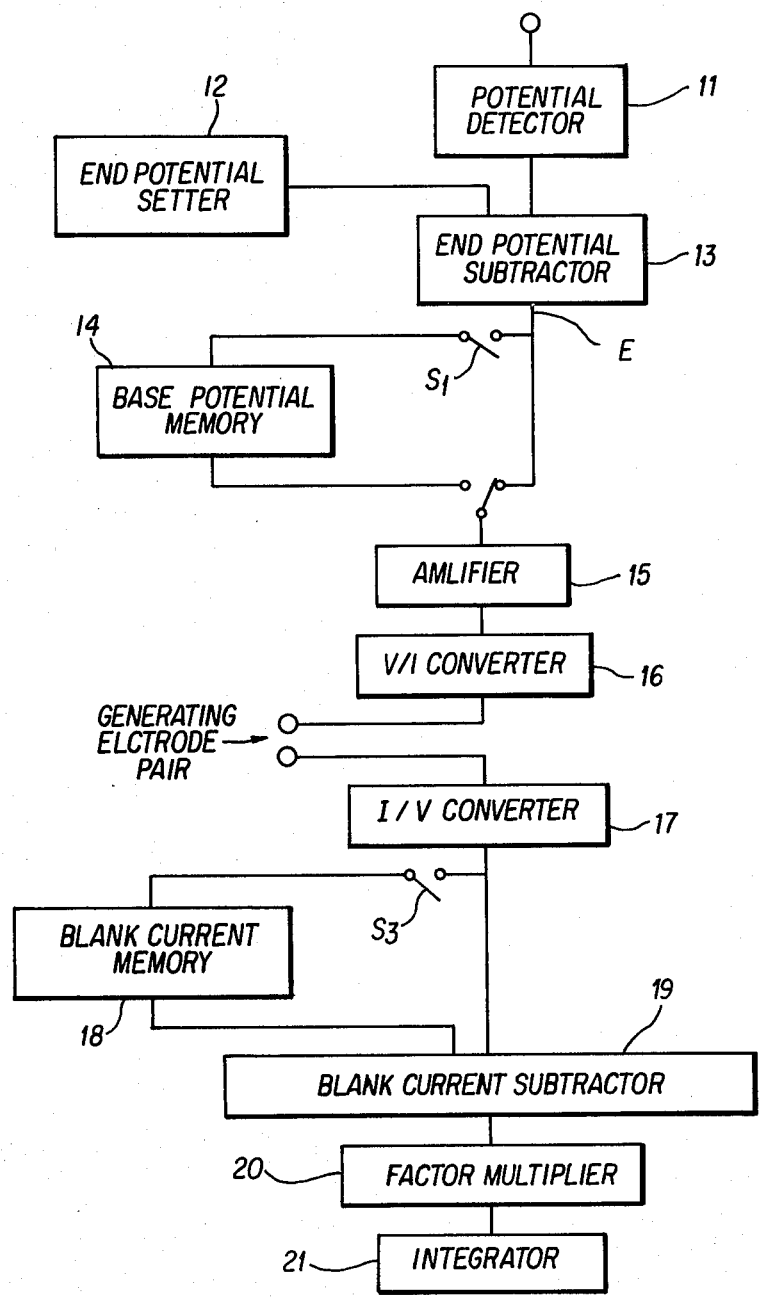
FIG. 2 is a block diagram showing one example of a coulometric titration unit shown in FIG. 1.
Figure 3:
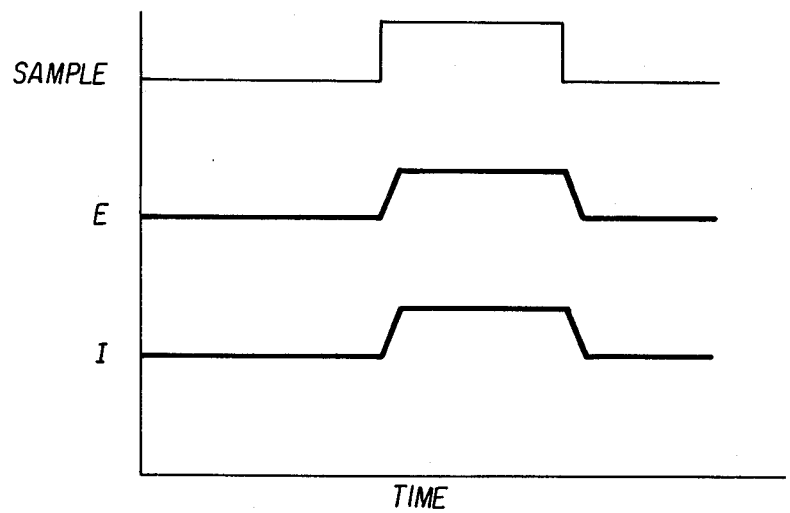
FIG. 3 is a graph showing variations in the potential of the electrolyte and in the current flowing between operation electrodes of a prior art coulometric titration method not using a waiting step.

Turning now to FIG. 2 showing a block diagram of one example of the coulometric titration unit 10 shown in FIG. 1, a potential detected by a potential detector 11, and an end potential from an end potential setter 12 are applied to an end potential subtractor 13 to obtain a potential difference $\Delta E$ as its output. This potential difference $\Delta E$ is applied to a base potential memory circuit 14 or an amplifier 15 respectively through switches $S_1$ and $S_2$. The base potential memory circuit 14 integrates the potential difference applied thereto to calculate and store the mean value thereof.

The amplifier 15 amplifies the potential difference $\Delta E$ or the output of the base potential memory circuit applied via transfer switch $S_2$ to apply its output to a V/I converter 16 which converts impressed voltage into current proportional thereto and passed across the generating electrodes. Further, this current is converted into voltage by an I/V converter 17 and the voltage is applied to a blank current memory circuit 8 through a switch $S_3$ and to a blank current subtractor 19. The blank current memory device 18 stores the applied voltage and then applies the stored voltage to the blank current subtractor 19. Thus, the blank current subtractor 19 receives the outputs of the I/V converter 17 and the blank current memory circuit 18 to produce a difference therebetween as an output which is converted into the quantity of the composition to be titrated by a factor multiplier 20. This quantity is displayed on the display device 11a shown in FIG. 1 after being integrated by an integrator 21.

The operation of the apparatus will now be described with reference to FIGS. 1 and 2. Firstly, various portions of the apparatus are brought to predetermined temperatures while supplying the carrier gas from the source thereof. As the potential of the electrolyte varies as a result of introduction of the carrier gas, the potential of the electrolyte is detected to pass blank current proportional to the difference between A preset end point potential and the detected potential across the generating electrodes so as to maintain the potential of the electrolyte at the end point potential. When the apparatus reaches a stable state, the blank current becomes constant.

In the block diagram shown in FIG. 2, the potential of the electrolyte is detected by the potential detector 11 via the detection electrode and applied to the end potential subtractor 13. At this time switch $S_1$ is open. The output $\Delta E$ of the subtractor 13 is applied to the V/I converter 16 via amplifier 15 to be converted into current passed between the pair of generating electrodes. Since, at this time switch $S_3$ is open, the outputs of the I/V converter 17 and of the blank current memory circuit 18 are applied to the blank current substrator 19, and the output thereof is applied to the factor multiplier 20. Although not shown, a gate circuit is interposed between the factor multiplier 20 and the integrator 21 and this gate circuit is disenabled until the titration process is commenced so that the integrator 21 and the display device 11a would not operate.

In this invention, the above described process is termed a balancing step in which preparation for the measurement is completed.

In the actual measurement, prior to the introduction of a composition to be titrated into the electrolyte, the value of the blank current passed between the generation electrodes is switched from a value proportional to the difference between the end potential up to that time and the detected potential to a steady or mean blank current during the balancing step.

More particularly, instead of determining the current to be passed between the generating electrodes in accordance with the detected potential of the electrolyte, and irrespective of the value of the detected potential, a current having the same value as that of a mean blank current which has been brought to a steady state during the stabilizing process or as that of the blank current which has been flowing immediately prior to the switching. This switching is effective to compensate for the variation in the electrolyte potential caused by the introduction of the carrier gas.

In this description, a process in which a blank current is passed having a value not depending upon the electrolyte potential is termed a waiting step, and the injection of the sample into the reaction tube is commenced during the waiting step.

In the block diagram shown in FIG. 2, the switch $S_1$ is closed when the balancing step has been completed to apply the output of the end potential subtractor 13 to the base potential memory circuit 14 for a definite interval, for example 10 minutes, for calculating and storing the mean value of the output $\Delta E$ of the end potential subtractor 13. Then, switch $S_1$ is opened and the switch $S_2$ is thrown to the lefthand side to continuously apply the potential stored in the base potential memory circuit 14 to the amplifier 15 via the transfer switch $S_2$ during the entire waiting step whereby a constant blank current is passed between the generating electrodes during the waiting step. The switch $S_3$ is closed concurrently with the throwing of the switch $S_2$ to the side of the base potential memory circuit 14 for storing the output of the I/V converter 17 in the blank current memory circuit 18 for a short time, for example one second, and then opened. During the waiting step, as the gate circuit interposed between the factor multiplier 20 and the integrator 21 is disenabled or opened, the integrator 21 and the display device 11a do not operate.

It is advantageous to effect the switching of the blank current to the waiting step at a time immediately prior to the introduction of the composition to be titrated into the electrolyte. However, in the case of a manual operation it is preferable to commence the injection of the sample into the reaction tube immediately after the switching of the blank current. On the other hand, in the case of an automatic operation it is advantageous to automatically switch the blank current by an electric signal which initiates the injection of the sample into the reaction tube.

During the waiting step, the composition to be titrated and introduced into the electrolyte is not titrated in any appreciable extent but merely accumulates in the electrolyte. Usually, the waiting step is continued until at least one half of the sample is injected. Since the waiting step is provided for the purpose of accumulating the composition to be titrated in the electrolyte, as the injection speed of the composition to be titrated into the reaction tube is small, the waiting step is generally lengthened so as to cause much higher percentage of the composition to accumulate in the electrolyte. Where the injection speed of the composition is very low, it is preferred to elongate the period of the waiting step until all quantity of the injected composition has been introduced into the electrolyte. However, it is nonsense to continue the waiting step beyond the completion of the introduction of the entire quantity of the composition into the electrolyte because this causes measurement errors.

Upon completion of a predetermined waiting step, current is again passed between the generating electrodes in accordance with the difference between the electrolyte potential and a preset end potential, while at the same time, the difference between the titration current and the blank current is integrated. This process is herein termed a titration step.

In the block diagram shown in FIG. 2, the switch $S_2$ is transferred when the waiting cycle completes to switch the input to the amplifier 15 from the output of the base potential memory circuit 14 to the output of the end potential subtractor 13. The switch $S_3$ is still maintained at the OFF state. Accordingly, the outputs of the I/V converter 17 and the blank current memory circuit 18 are applied to the blank current subtractor 19 to obtain an output corresponding to the difference between both outputs. As the gate circuit between the factor multiplier 20 and the integrator 21 is enabled concurrently with the throwing of the switch $S_2$ to the side of the end potential subtractor 13, the output of the blank current subtractor 19 is converted into the quantity of the composition to be titrated by the factor multiplier 20 and then integrated by the integrator 21 and displayed by the display device 11a.

The titration step is continued until a detected potential coincides with a preset end potential.

Figure 4:
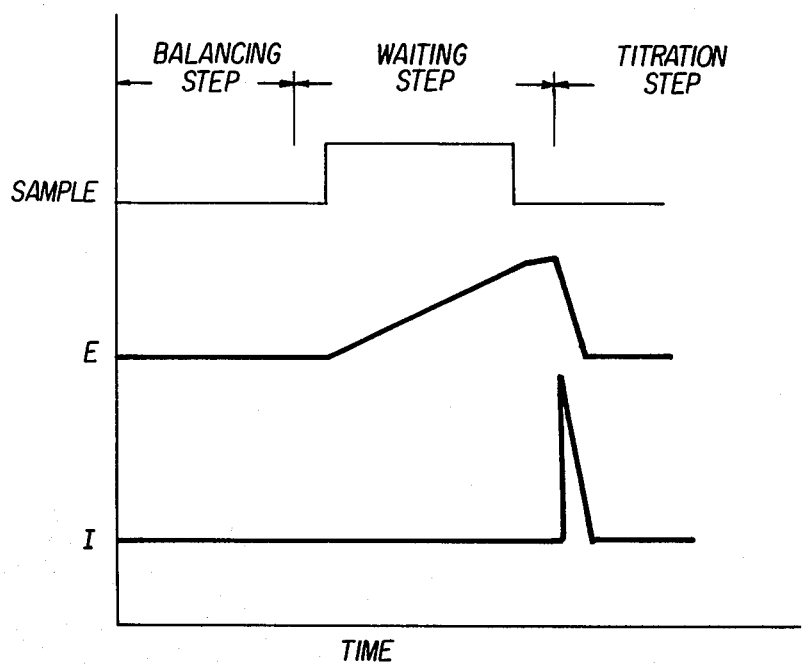
FIG. 4 is a graph showing variations in the potential of the electrolyte and in the current flowing between operation electrodes which appear in the method of this invention.

FIG. 4 diagrammatically shows variations in the electrolyte potential and in the current flowing between the generating electrodes. As shown when the balancing step is finished and the waiting step begins, the current flowing between the generating electrodes is maintained at a constant value not influenced by the electrolyte potential, for example at the mean value at the end of the balancing step. During the waiting step, the sample is injected into the apparatus at a constant speed. Then, the composition to be titrated is introduced into the electrolyte and accumulates therein so that the electrolyte potential increases gradually. As the introduction of the composition to be titrated into the electrolyte ceases, rise of the potential also ceases. When the waiting step is completed and the titration step begins, current proportional to the electrolyte potential flows between the generating electrodes. As the composition to be titrated in the electrolyte is consumed rapidly by the titration, the electrolyte potential also decreases rapidly with the result that the current flowing between the generating electrodes also decreases. When all quantity of the composition to be titrated is consumed the potential and current become equal to those of the balancing step.

As above described, according to this invention since the coulometric titration is effected after a composition to be titrated and introduced into an electrolyte has accumulated for a predetermined interval, a large titration current flows between generating electrodes. Accordingly, measurement error is small and a high accuracy measurement can take place with a sample containing only a minute quantity of a composition to be titrated.

To have better understanding of the invention the following example is given but should not be construed to limit the scope of the invention.

EXAMPLE

Digital minute quantity sulfur analyzing apparatus, of the Type TS-20 manufactured by the assignee was modified and used as the apparatus shown in FIGS. 1 and 2. Modified points are provision of a dehumidifier in a gas conduit interconnecting the reaction tube and the titration cell, and switching the current supplied to the generating electrode pair between current proportional to the difference between a detected potential and a preset potential and constant current independent of the detected potential. As the dehumidifier was used a small gas washing bottle charged with a liquid mixture of 8nl of phosphoric acid and 2nl of water. Gas was admitted at a depth of about 3 cm of the liquid.

With this apparatus, analysis of sulfur content was made on a sample prepared by dissolving n-hexyl sulfide $[CH_3(CH_2)_5]_2S$ in a high grade n-hexan utilized as a reagent.

In the analysis, the apparatus was brought to a stable state by passing a gaseous mixture of oxygen and argon and the current supplied to the generating electrode pair was switched to a constant current. 30 minutes after the switching, 200 $\mu$l of the sample was injected into the reaction tube. The sample was injected for 2.5 minutes with an automatic injector (Type MF-01, manufactured by the assignee). Because the constant current was used, the current had the same magnitude as that flowing between the generating electrodes immediately before the switching. After elapse of one minute subsequent to the completion of the injection, the current supplied to the generating electrode pair was switched from the constant current to a current proportional to the difference between the detected potential and the set potential so as to coulometrically titrate with iodine the sulfur dioxide formed by the reaction.

The results of the titration are shown in the following table.

| Sample | | Measured value (quantity of $SO_2$ formed before correction) | |
|---|---|---|---|
| | | with awaiting step | without awaiting step |
| Sulfur content | 0.2 $\mu$g/ml | 25 ng | 25 ng |
| Sulfur content | 0.1 $\mu$g/ml | 12 ng | 12 ng |
| | 0.075 $\mu$g/ml | 9 ng | 6 ng |
| | 0.05 $\mu$g/ml | 6 ng | 1 ng |
| | 0.025 $\mu$g/ml | 3 ng | 0 |
| n-hexan | | 1 ng | 0 |

As can be clearly noted from this table the method of this invention is extremely effective to measure extremely small quantity of sulfur of less than 0.1 $\mu$g/ml.

We claim:
1. A coulometric titration method comprising the steps of:
   balancing an electrolyte potential in a titration cell by detecting said potential while passing carrier gas and passing a current between generating electrodes immersed in the electrolyte so as to elimi- nate potential differences between the detected potential and a preset potential;

passing during a predetermined waiting time, a constant current between the generating electrodes not dependent upon the electrolyte potential;

introducing a composition to be titrated into the titration cell together with the carrier gas during the predetermined waiting time;

titrating by measuring the electrolyte potential and passing a current between the generating electrode so as to eliminate potential difference between the detected potential and the set potential;

integrating the difference between current flowing between the generating electrodes during the titration step and a blank current;

calculating the quantity of composition to be titrated introduced into the titration cell in accordance with an integrated value determined by said integrating step.

2. The coulometric titration method according to claim 1 wherein the current passed through the generating electrodes during the waiting step is equal to a mean value of the current passed through the generation electrodes under a steady state of the balancing step.

3. The coulometric titration method according to claim 1 wherein the current passed through the generation electrodes during the waiting step has a magnitude equal to that which flows between the generating electrodes at the end of the balancing step.

4. The coulometric titration method according to claim 1, 2 or 3 wherein the titration step is commenced after more than one half of the composition to be titrated has been introduced into the cell.

5. The coulometric titration method according to claim 1, 2 or 3 wherein the titration step is commenced when the entire quantity of the component to be titrated has been introduced into the titration cell.

* * * * *